US011213511B2

(12) United States Patent
Jung et al.

(10) Patent No.: US 11,213,511 B2
(45) Date of Patent: Jan. 4, 2022

(54) COMPOSITION FOR PREVENTING OR TREATING SARS CORONAVIRUS 2 INFECTION DISEASE

(71) Applicant: Syntekabio, Inc., Daejeon (KR)

(72) Inventors: Jong Sun Jung, Daejeon (KR); Jong Hui Hong, Seoul (KR); Dong Myung Kim, Daejeon (KR); Bong Hwan Park, Gyeonggi-do (KR); Young Bae Ryu, Daejeon (KR); Hyung Jun Kwon, Daejeon (KR); In Chul Lee, Daejeon (KR); Ji Young Park, Daejeon (KR)

(73) Assignee: Syntekabio, Inc., Daejeon (KR)

( * ) Notice: Subject to any disclaimer, the term of this patent is extended or adjusted under 35 U.S.C. 154(b) by 0 days.

(21) Appl. No.: 17/205,809

(22) Filed: Mar. 18, 2021

(65) Prior Publication Data
US 2021/0361619 A1    Nov. 25, 2021

Related U.S. Application Data

(63) Continuation of application No. PCT/KR2020/014348, filed on Oct. 20, 2020.

(30) Foreign Application Priority Data

| May 20, 2020 | (KR) | 10-2020-0060160 |
| Jul. 23, 2020 | (KR) | 10-2020-0091814 |
| Sep. 7, 2020 | (KR) | 10-2020-0113852 |

(51) Int. Cl.
| A61K 31/404 | (2006.01) |
| A61K 31/4152 | (2006.01) |
| A61K 9/00 | (2006.01) |
| A61P 31/14 | (2006.01) |

(52) U.S. Cl.
CPC .......... *A61K 31/404* (2013.01); *A61K 9/0043* (2013.01); *A61K 9/0053* (2013.01); *A61K 9/0073* (2013.01); *A61K 31/4152* (2013.01); *A61P 31/14* (2018.01)

(58) Field of Classification Search
CPC .................................................. A61K 31/404
See application file for complete search history.

(56) References Cited

U.S. PATENT DOCUMENTS

| 2006/0257852 | A1 | 11/2006 | Rappuoli et al. |
| 2007/0099855 | A1 | 5/2007 | Cinatl |
| 2009/0297436 | A1* | 12/2009 | Garcia-Martinez ..... A61P 35/00 424/1.11 |
| 2011/0243924 | A1 | 10/2011 | Beleta Supervia |
| 2020/0360381 | A1* | 11/2020 | Yang .................. A61K 31/4045 |

FOREIGN PATENT DOCUMENTS

| KR | 10-2006-0025549 A | 3/2006 |
| KR | 10-2009-0001260 A | 1/2009 |
| KR | 10-2009-0114401 A | 11/2009 |
| KR | 10-1913789 A | 10/2018 |

OTHER PUBLICATIONS

Djokovic et al., "An integrative in silico drug repurposing approach for identification of potential inhibitors of SARS-CoV-2 main protease," p1-38 (2020). Retrieved from the Internet at: https://chemrxiv.org/articles/preprint/An_Integrative_in_Silico_Drug_Repurposing_Approach_for_Identification_of_Potential_Inhibitors_of_SARS-CoV-2_Main_Protease/12578672.
Jin et al., "Structure of M pro from COVID-19 virus and discovery of its inhibitors," Nature (2020).
Li et al., "Therapeutic options for the 2019 novel coronavirus (2019-nCoV)," Nat Rev Drug Discov., 19(3):149-150 (2020).
Muramatsu et al., "Autoprocessing mechanism of severe acute respiratory syndrome coronavirus 3C-like protease(SARS-CoV 3CLpro) from its polyproteins," FEBS J. 280(9):2002-2013 (2013).
Senathilake et al, 'Virtual screening of inhibitors against spike glycoprotein of SARS-CoV-2: drug repurposing approac, 1-10 (2020).
Senathilake et al, 'Virtual screening of inhibitors against spike glycoprotein of SARS-CoV-2: a drug repurposing approach, 1-16 (2020).
Wang et al., "Subunit Vaccines Against Emerging Pathogenic Human Coronaviruses" Front Microbiol., 11(298):1-19 (2020).
Wu et al., "Analysis of therapeutic targets for SARS-CoV-2 and discovery of potential drugs by computational methods," Feb Acta Pharmaceutica Sinica B 10(5):766-788 (2020).

* cited by examiner

*Primary Examiner* — Rei Tsang Shiao
(74) *Attorney, Agent, or Firm* — Marshall, Gerstein & Borun LLP

(57) ABSTRACT

Disclosed is a pharmaceutical composition for preventing or treating severe acute respiratory syndrome coronavirus 2 infection disease, the composition comprising a compound represented by a Chemical Formula 1, or a pharmaceutically acceptable salt thereof, as an active ingredient.

19 Claims, 8 Drawing Sheets

[FIG.1]
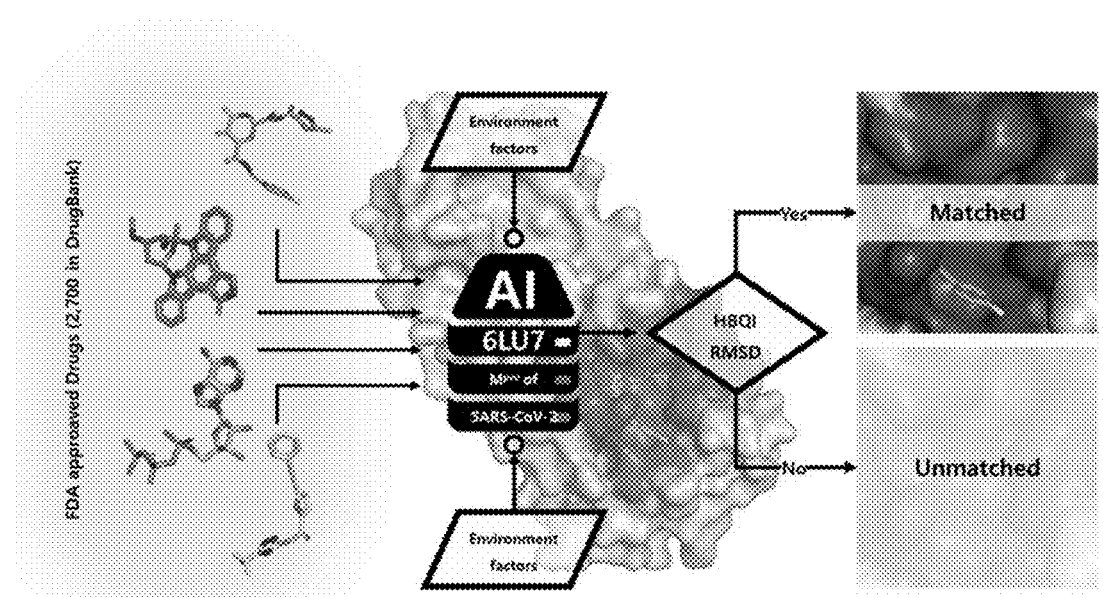

[FIG.2]
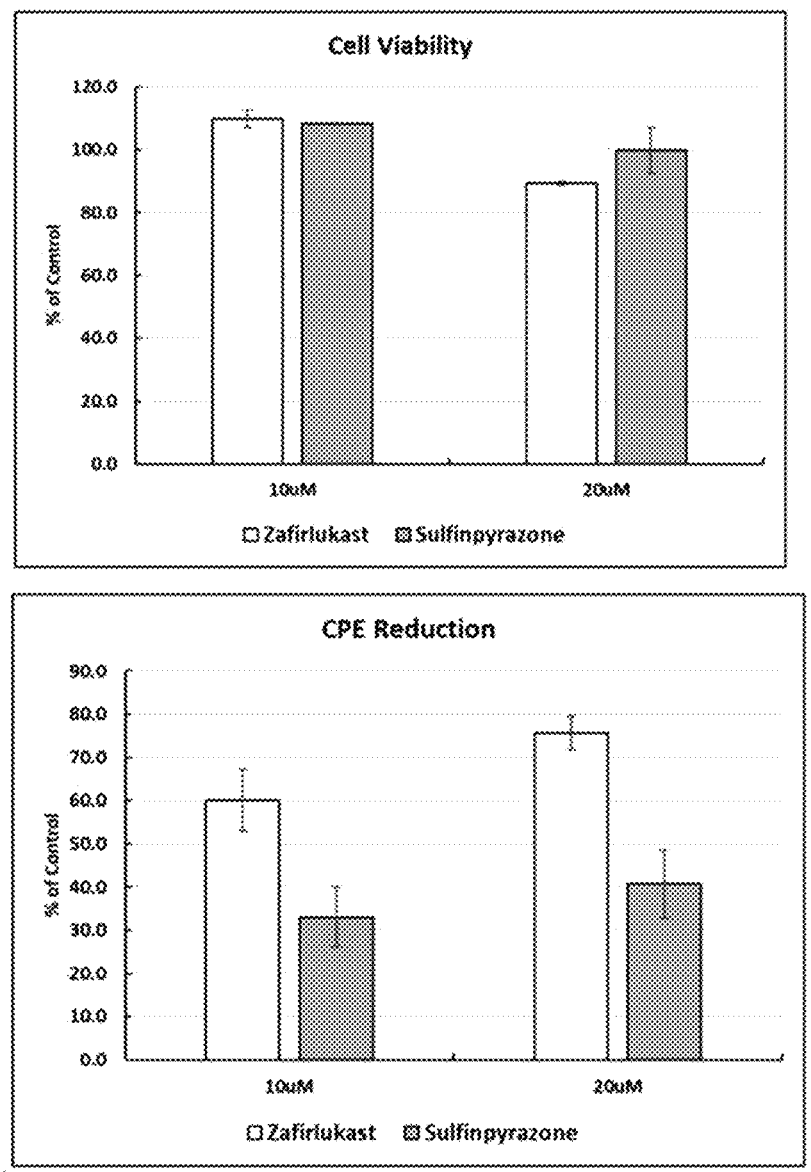

[FIG.3]
| Drug Name | Cell Morphology ||
| --- | --- | --- |
| | Normal | Virus |
| Control | 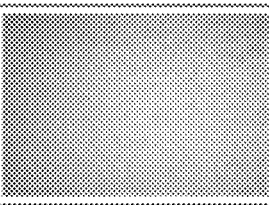 | 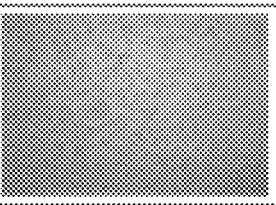 |
| | 10 μM | 20 μM |
| Zafirlukast | 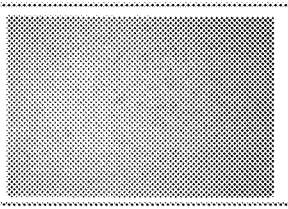 | 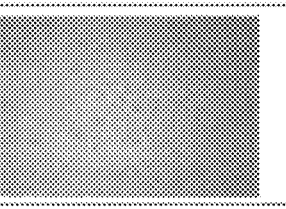 |
| Sulfinpyrazone | 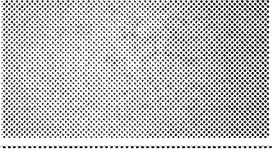 | 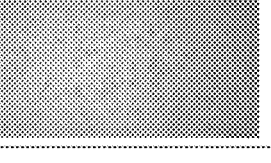 |

[FIG.4]
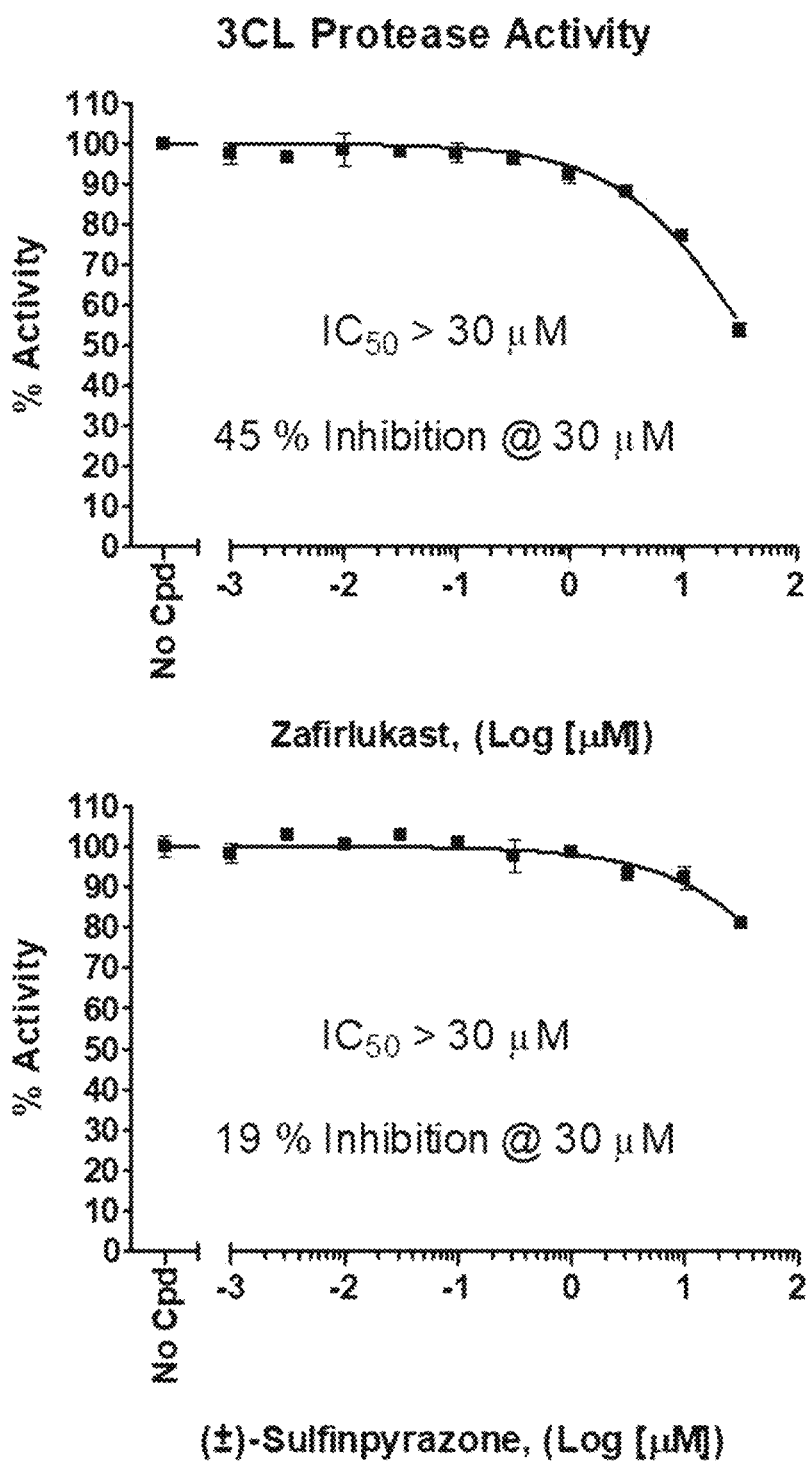

[FIG.5]
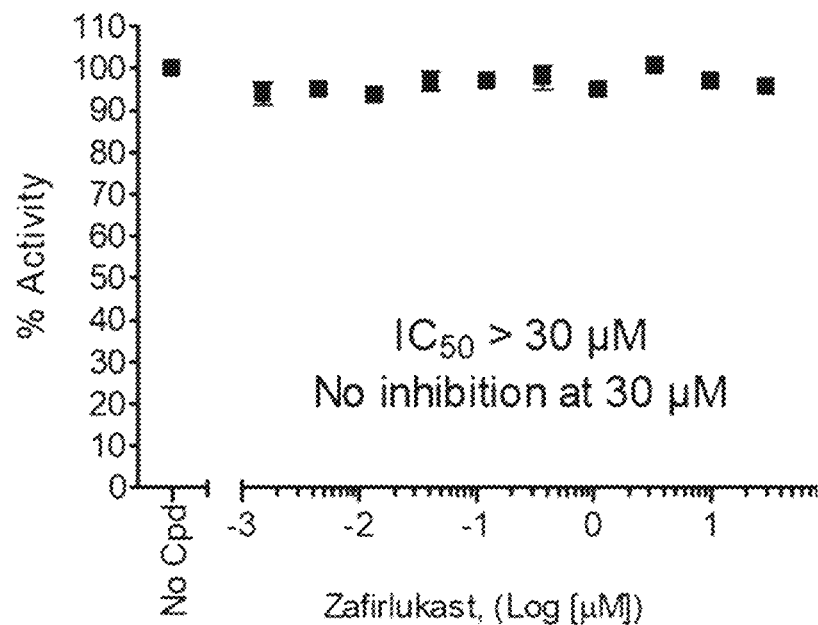
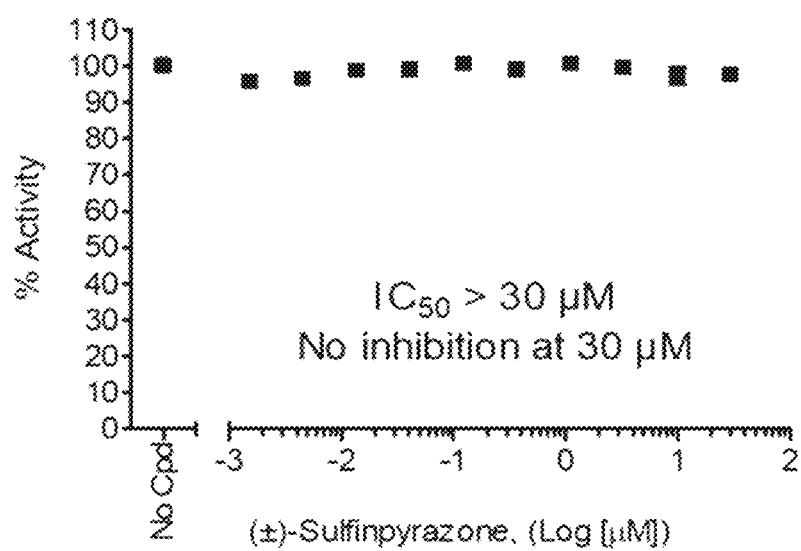

[FIG.6]
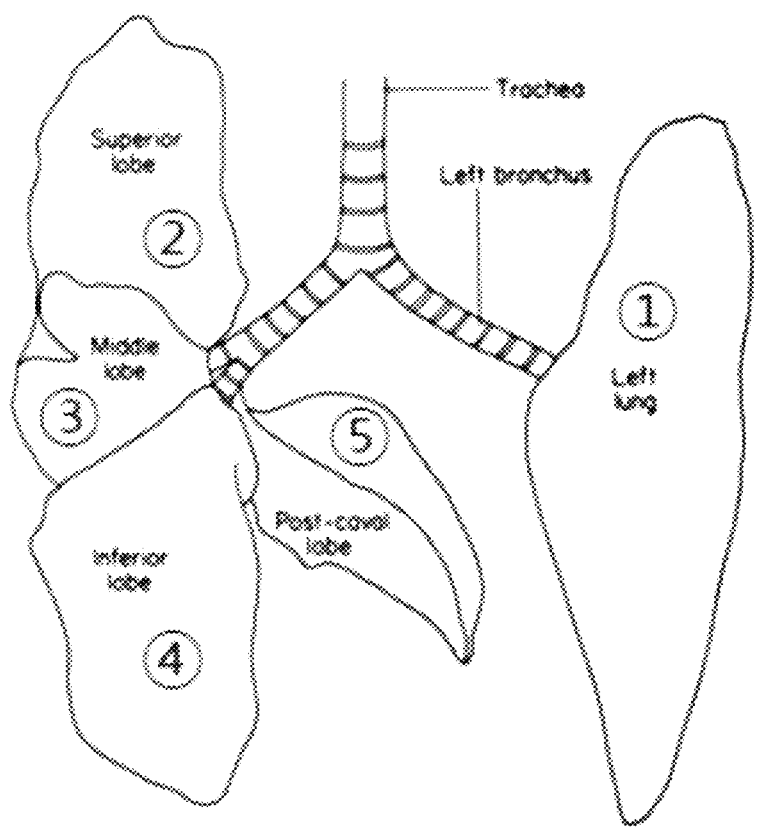

[FIG.7]
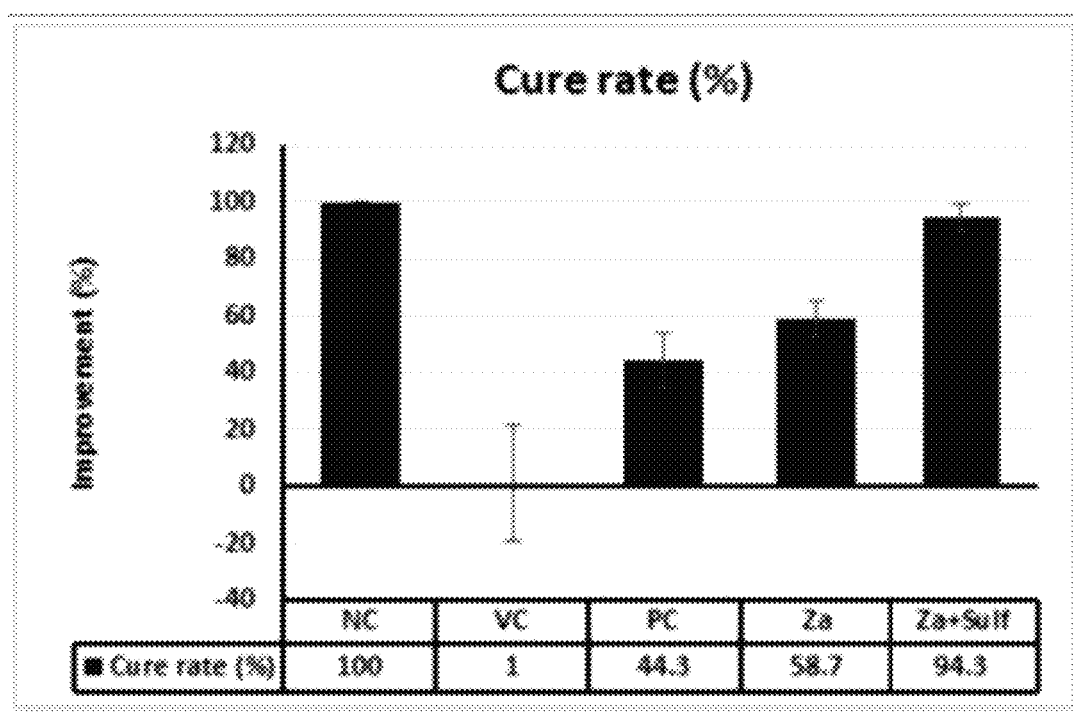

[FIG.8]
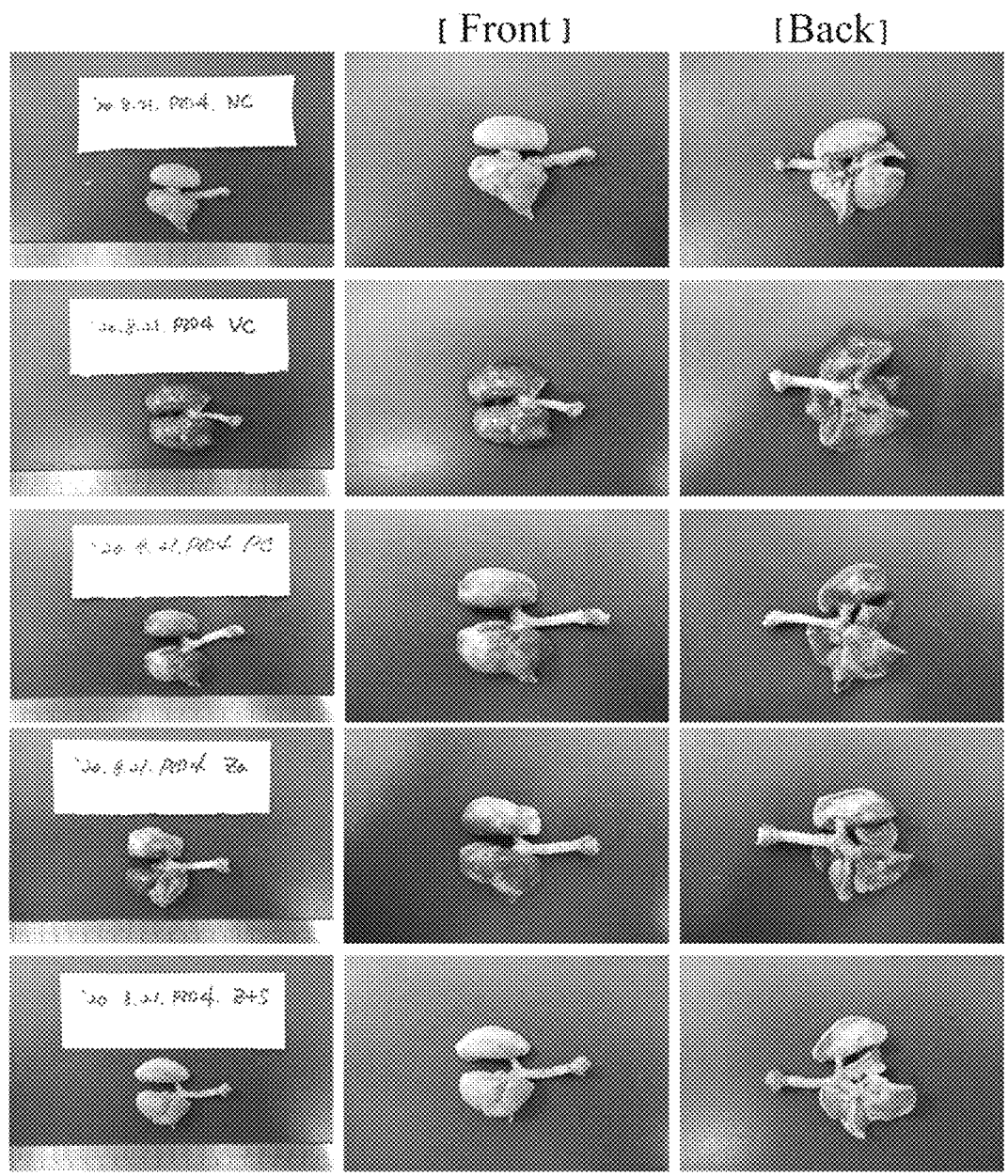

COMPOSITION FOR PREVENTING OR TREATING SARS CORONAVIRUS 2 INFECTION DISEASE

TECHNICAL FIELD

The present disclosure relates to a composition for preventing or treating severe acute respiratory syndrome coronavirus 2 infection or diseases caused by severe acute respiratory syndrome coronavirus 2 infection.

BACKGROUND ART

The severe acute respiratory syndrome coronavirus 2 (COVID-19, SARS-CoV-2, 2019-nCoV) had first outbreak in Wuhan, China in December 2019 and then has spread to China and around the world. Accordingly, the World Health Organization (WHO) declared Public Health Emergency of International Concern (PHEIC) for severe acute respiratory syndrome coronavirus 2, and on Mar. 11, 2020, declared a global pandemic of severe acute respiratory syndrome coronavirus 2 following the Hong Kong flu (1968) and novel swine-origin influenza A (H1N1) (2009). People is infected with severe acute respiratory syndrome coronavirus 2 when droplets (saliva) of infected people invade the respiratory tract or the mucous membranes of the eyes, nose and mouth. When infected, after an incubation period of 2 to 14 days (estimated), respiratory symptoms such as fever, coughing or shortness of breath, and pneumonia occur as the main symptoms, but asymptomatic infection cases are rare.

Coronaviruses are classified into $\alpha$, $\beta\beta$, $\gamma\gamma$ and $\delta\delta$ groups according to the difference in nucleotide sequences of RNA replication and transcription enzyme (RdRp). severe acute respiratory syndrome coronavirus 2 virus together with the SARS-CoV and MERS-CoV viruses infects people, belonging to group $\tau3$ (Subunit Vaccines Against Emerging Pathogenic Human Coronaviruses. Wang N, Shang J, Jiang S, Du L. Front Microbiol. 2020 Feb. 28; 11:298.). The nucleotide sequence of severe acute respiratory syndrome coronavirus 2 is identical with SARS-CoV and MERS-CoV, by 80% and 50%, respectively (Wu C. et al. Analysis of therapeutic targets for SARS-CoV-2 and discovery of potential medicaments by computational methods. 2020 February Acta Pharmaceutica Sinica B).

Coronavirus is a positive single-stranded RNA virus of 26 to 32 kb in length. When the coronavirus enters the host through the host cell's receptor, the coronavirus produces two large polyproteins; pp1a (486 kDa), and pp1ab (790 kDa), and then, therefrom, produces the protease of the virus itself; produces enzymes required for viral transcription and replication using 3CL protease (also referred to as 3CLpro, or Mpro); and produces 16 non-structural proteins comprising RdRp, Helicase, ribonucleoclease, 3CLpro, etc. (Autoprocessing mechanism of severe acute respiratory syndrome coronavirus 3C-like protease (SARS-CoV 3CLpro) from its polyproteins. Muramatsu T, Kim Y T, Nishii W, Terada T, Shirouzu M, Yokoyama S. FEBS J. 2013 May;280(9)):2002-13.doi: 10.1111).

3CLpro is a protein with a molecular weight of 34 kDa (306 amino acids), and its initial abundance is reported to be automatically cut out from pp1a and pp1ab (autoprocessing) (Autoprocessing mechanism of severe acute respiratory syndrome coronavirus 3C-like protease (SARS-CoV 3CLpro) from its polyproteins. Muramatsu T, Kim Y T, Nishii W, Terada T, Shirouzu M, Yokoyama S. FEBS J. 2013 May; 280(9):2002-13.doi: 10.1111). 3CLpro is a dimer structure consisting of domains I, II, and III. In 3CLpro, an active site (substrate binding site) is located in the cleft between domains I and II. As for the active site, the amino acid sequence and three-dimensional structure are well preserved between coronaviruses (structurally identical to SARS-CoV by 96%). Recently, Jin Z. group in China reported the structure of severe acute respiratory syndrome coronavirus 2 3CLpro (Protein Data Bank ID 6LU7). The structural differences between the 12 coronavirus 3CLpro occur in domain III and surface loops, and the active sites were highly conserved (Structure of Mpro from severe acute respiratory syndrome coronavirus 2 virus and discovery of its inhibitors. Jin Z, Du X, Xu Y, Deng Y, Liu M, Zhao Y, Zhang B, Li X, Zhang L, Peng C, Duan Y, Yu J, Wang L, Yang K, Liu F, Jiang R, Yang X, You T, Liu X, Yang X, Bai F, Liu H, Liu X, Guddat L W, Xu W, Xiao G, Qin C, Shi Z, Jiang H, Rao Z, Yang H. Nature. 2020 Apr. 9.doi: 10.1038/s41586-020-2223-y).

As described above, 3CLpro is one of the important targets of coronavirus treatment agents because the amino acid sequence and structure of 3CLpro has little change between coronaviruses and, above all, the function of 3CLpro is essential for viral growth. All of severe acute respiratory syndrome coronavirus 2 treatment agents such as Lopinavir (phase 3: NCT04252274, NCT04251871, NCT04255017, ChiCTR2000029539), Ritonavir (phase 3: NCT04251871, NCT04255017, NCT04261270), and Darunavir (phase 3: NCT04252274) which are currently being developed target 3CLpro. These medicaments were originally approved by the FDA as protease inhibitors of HIV (Human Immunodeficiency Virus) (Therapeutic options for the 2019 novel coronavirus (2019-nCoV). Li G, De Clercq E. Nat Rev Drug Discov. 2020 March;19(3):149-150.doi: 10.1038).

A pharmaceutical composition for ameliorating or treating coronavirus infectious diseases comprises a compound for treating diseases caused by coronavirus infection as disclosed in Korean Patent No. 1913789. U.S. Patent Application Publication No. 2006-0257852 discloses a technology for severe acute respiratory syndrome coronavirus. However, there is no disclosed composition for the prevention or treatment of coronavirus infection disease, which contains, as an active ingredient, an inhibitor of the coronavirus 3CL protease activity according to the present disclosure.

DISCLOSURE

Technical Purpose

One purpose of the present disclosure is to provide a pharmaceutical composition for preventing or treating severe acute respiratory syndrome coronavirus 2 infection disease, the composition comprising a compound represented by a Chemical Formula 1, or a pharmaceutically acceptable salt thereof, as an active ingredient.

Another purpose of the present disclosure is to provide a pharmaceutical composition for preventing or treating severe acute respiratory syndrome coronavirus 2 infection disease, the composition comprising a compound represented by a Chemical Formula 2, or a pharmaceutically acceptable salt thereof, as an active ingredient.

Another purpose of the present disclosure is to provide a pharmaceutical composition for preventing or treating severe acute respiratory syndrome coronavirus 2 infection disease, the composition comprising a compound represented by the Chemical Formula 1, or a pharmaceutically acceptable salt thereof, and a compound represented by the Chemical Formula 2, or a pharmaceutically acceptable salt thereof, as an active ingredient.

Another purpose of the present disclosure is to provide a food composition for preventing or ameliorating severe acute respiratory syndrome coronavirus 2 infection disease, the composition comprising a compound represented by the Chemical Formula 1, or a food acceptable salt thereof.

Another purpose of the present disclosure is to provide a food composition for preventing or ameliorating severe acute respiratory syndrome coronavirus 2 infection disease, the composition comprising a compound represented by the Chemical Formula 2, or a food acceptable salt thereof.

Another purpose of the present disclosure is to provide a food composition for preventing or ameliorating severe acute respiratory syndrome coronavirus 2 infection disease, the composition comprising a compound represented by the Chemical Formula 1, or a food acceptable salt thereof, and a compound represented by the Chemical Formula 2, or a food acceptable salt thereof.

Another purpose of the present disclosure is to provide a method for treating severe acute respiratory syndrome coronavirus 2 infection disease, the method comprising administering a therapeutically effective amount of a compound represented by the Chemical Formula 1, or a pharmaceutically acceptable salt thereof, to a subject in need thereof.

Another purpose of the present disclosure is to provide a method for treating severe acute respiratory syndrome coronavirus 2 infection disease, the method comprising administering a therapeutically effective amount of a compound represented by the Chemical Formula 2, or a pharmaceutically acceptable salt thereof, to a subject in need thereof.

Another purpose of the present disclosure is to provide a method for treating severe acute respiratory syndrome coronavirus 2 infection disease, the method comprising administering a therapeutically effective amount of a compound represented by the Chemical Formula 1, or a pharmaceutically acceptable salt thereof, and a therapeutically effective amount of a compound represented by the Chemical Formula 2, or a pharmaceutically acceptable salt thereof, to a subject in need thereof.

Another purpose of the present disclosure is to provide an anti-severe acute respiratory syndrome coronavirus 2 composition comprising a compound represented by the Chemical Formula 1, or a pharmaceutically acceptable salt thereof, as an active ingredient.

Another purpose of the present disclosure is to provide an anti-severe acute respiratory syndrome coronavirus 2 composition comprising a compound represented by the Chemical Formula 2, or a pharmaceutically acceptable salt thereof, as an active ingredient.

Another purpose of the present disclosure is to provide an anti-severe acute respiratory syndrome coronavirus 2 composition comprising a compound represented by the Chemical Formula 1, or a pharmaceutically acceptable salt thereof, and a compound represented by the Chemical Formula 2, or a pharmaceutically acceptable salt thereof as an active ingredient.

Another purpose of the present disclosure is to provide an inhibitor for inhibiting activity of 3CL protease, the inhibitor comprising a compound represented by the Chemical Formula 1, or a pharmaceutically acceptable salt thereof.

Another purpose of the present disclosure is to provide an inhibitor for inhibiting activity of 3CL protease, the inhibitor comprising a compound represented by the Chemical Formula 2, or a pharmaceutically acceptable salt thereof.

Another purpose of the present disclosure is to provide an inhibitor for inhibiting activity of 3CL protease, the inhibitor comprising a compound represented by the Chemical Formula 1, or a pharmaceutically acceptable salt thereof, and a compound represented by the Chemical Formula 2, or a pharmaceutically acceptable salt thereof.

Technical Solution

The present inventors have discovered a compound that is effective in preventing or treating severe acute respiratory syndrome coronavirus 2 infection disease and have confirmed inhibitory effect thereof on severe acute respiratory syndrome coronavirus 2. Thus, the present disclosure has been completed.

In one aspect of the present disclosure, the present disclosure provides a pharmaceutical composition for preventing or treating severe acute respiratory syndrome coronavirus 2 infection disease, the composition comprising a compound represented by a following Chemical Formula 1, or a pharmaceutically acceptable salt thereof, as an active ingredient.

[Chemical Formula 1]

The compound represented by the Chemical Formula 1 is Zafirlukast, and an IUPAC name thereof is cyclopentyl3-{2-methoxy-4-[(o-tolylsulfonyl)carbamoyl]benzyl}-1-methyl-1H-indol-5-ylcarbamate.

In the present disclosure, the compound represented by the Chemical Formula 1 may inhibit 3CL protease activity. Accordingly, the compound of the Chemical Formula 1 may be utilized to inhibit virus proliferation in host cells (subject) already infected with severe acute respiratory syndrome coronavirus 2.

In another aspect of the present disclosure, the present disclosure provides a pharmaceutical composition for preventing or treating severe acute respiratory syndrome coronavirus 2 infection disease, the composition comprising a compound represented by a following Chemical Formula 2, or a pharmaceutically acceptable salt thereof, as an active ingredient.

[Chemical Formula 2]

The compound represented by the Chemical Formula 2 is Sulfinpyrazone, and an IUPAC name thereof is 1,2-diphenyl-4-[2-(phenylsulfinyl)ethyl]pyrazolidine-3,5-dione. The sulfinpyrazone is generally known as a platelet aggregation inhibitor. Conventionally, effect thereof on inhibiting 3CL protease activity or effect of anti-severe acute respiratory syndrome coronavirus 2 thereof has not been disclosed.

In the present disclosure, the compound represented by the Chemical Formula 2 may inhibit 3CL protease activity. Thus, the compound of the Chemical Formula 2 may be used to inhibit virus proliferation in a host cell (subject) already infected with severe acute respiratory syndrome coronavirus 2.

In another aspect of the present disclosure, the present disclosure provides a pharmaceutical composition for preventing or treating severe acute respiratory syndrome coronavirus 2 infection disease, the composition comprising a compound represented by the following Chemical Formula 1, or a pharmaceutically acceptable salt thereof, and a compound represented by the following Chemical Formula 2, or a pharmaceutically acceptable salt thereof, as an active ingredient.

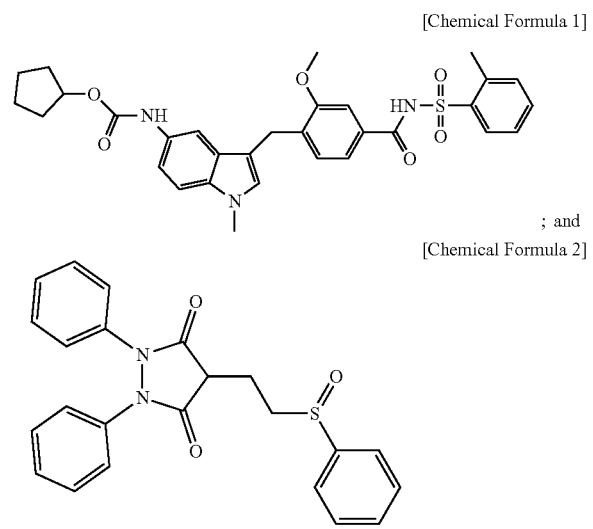

[Chemical Formula 1]

; and

[Chemical Formula 2]

In the present disclosure, the combined pharmaceutical composition comprising the compounds respectively represented by the Chemical Formulas 1 and 2 may inhibit 3CL protease activity. Thus, the combination of the compounds of the Chemical Formulas 1 and 2 has a synergistic effect and may be used to inhibit virus proliferation in host cells (subject) already infected with severe acute respiratory syndrome coronavirus 2.

In the present disclosure, the compound represented by the Chemical Formula 1 or the pharmaceutically acceptable salt thereof; and the compound represented by the Chemical Formula 2 or the pharmaceutically acceptable salt thereof may be mixed in a weight ratio of 1:99 to 99:1, but is not limited thereto.

Further, in the present disclosure, the compound represented by the Chemical Formula 1 or a pharmaceutically acceptable salt thereof; and a compound represented by the Chemical Formula 2 or a pharmaceutically acceptable salt thereof may be administered simultaneously, individually or sequentially in combination with each other, and may be administered single or multiple times. It is important to take into account all of the above factors and then administer the minimum amount at which the maximum effect may be obtained without side effects, based on the factors. This amount may be easily determined by a person skilled in the art.

Specifically, in the present disclosure, the composition comprising the compound of the Chemical Formula 1, the composition comprising the Chemical Formula 2, or the composition comprising the compounds of the Chemical Formulas 1 and 2 may inhibit a protein segmentation step that processes a protein related to proliferating of the virus in the subject after the subject is infected with severe acute respiratory syndrome coronavirus 2. This mechanism is distinguished from activity of inhibiting a first stage of the virus infection, and particularly, is different from the mechanism that inhibits binding (virus entry) for infection of the virus into the host cell (subject).

Hereinafter, the present disclosure will be described in detail.

The terminology used herein is for the purpose of describing particular embodiments only and is not intended to limit the present disclosure. As used herein, the singular forms "a" and "an" are intended to comprise the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

Unless otherwise defined, all terms comprising technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the present disclosure, anti-severe acute respiratory syndrome coronavirus 2 may refer to prevention, treatment or amelioration of a severe acute respiratory syndrome coronavirus 2 infection disease, i.e., of a severe acute respiratory syndrome coronavirus 2 infection or a disease caused by the severe acute respiratory syndrome coronavirus 2 infection. Further, anti-severe acute respiratory syndrome coronavirus 2 may be interpreted as comprising all actions that reduce the activity of viruses, comprising inhibition of proliferation, and killing of severe acute respiratory syndrome coronavirus 2 in a subject.

In the present disclosure, the "prevention" means any action that inhibits or delays infection of severe acute respiratory syndrome coronavirus 2 or a disease caused by severe acute respiratory syndrome coronavirus 2 infection via administration of the pharmaceutical composition. Further, the "treatment" refers to any action by which the symptoms of the severe acute respiratory syndrome coronavirus 2 infection or diseases caused by the severe acute respiratory syndrome coronavirus 2 infection are reduced or beneficially changed via the administration of the pharmaceutical composition.

The disease caused by severe acute respiratory syndrome coronavirus 2 infection may be a respiratory disease. The symptoms of the severe acute respiratory syndrome coronavirus 2 infection disease may appear, for example, after an incubation period of 2 to 14 days after viral infection. These symptoms comprise, for example, high fever, cough, shortness of breath, pneumonia, gastrointestinal symptoms such as diarrhea, organ insufficiency (renal failure, kidney dysfunction, etc.), septic shock, and in severe cases, death. Any symptom caused by the infection is comprised herein.

The compound represented by the Chemical Formula 1 or the compound represented by the Chemical Formula 2 in accordance with the present disclosure comprises not only a pharmaceutically acceptable salt thereof but also isomers, hydrates, and solvates thereof that may be prepared by conventional methods.

In the present disclosure, the pharmaceutically acceptable salt refers to a salt commonly used in the pharmaceutical industry. For example, the pharmaceutically acceptable salt may comprise inorganic ion salts made of calcium, potassium, sodium and magnesium, inorganic acid salts made of hydrochloric acid, nitric acid, phosphoric acid, bromic acid, iodic acid, perchloric acid and sulfuric acid; organic acid salts made of acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like; sulfonic acid salts made of methanesulfonic acid, ethanesulfonic acid, benzenesulfonic acid, p-toluenesulfonic acid and naphthalenesulfonic acid; amino acid salts made of glycine, arginine, lysine, and the like; and amine salts made of trimethylamine, triethylamine, ammonia, pyridine, picoline, etc. However, the types of salts meant in the present disclosure are not limited to these listed salts.

The pharmaceutically acceptable salt may be applied correspondingly to a food acceptable salt.

The pharmaceutical composition according to the present disclosure may additionally comprise an ingredient that does not increase medicament efficacy but is commonly used in pharmaceutical compositions to improve smell, taste, vision, and the like. Further, the pharmaceutical composition according to the present disclosure may additionally comprise a pharmaceutically acceptable additive. The pharmaceutically acceptable additives may comprise, for example, starch, gelatinized starch, microcrystalline cellulose, lactose, povidone, colloidal silicon dioxide, calcium hydrogen phosphate, lactose, mannitol, malt, arabic rubber, pregelatinized starch, corn starch, powdered cellulose, hydroxypropyl cellulose, Opadry, sodium starch glycolate, lead carnauba, synthetic aluminum silicate, stearic acid, magnesium stearate, aluminum stearate, calcium stearate, white sugar, dextrose, sorbitol, talc, and the like, but are not limited thereto. In addition, the pharmaceutical composition may comprise a substance having anti-severe acute respiratory syndrome coronavirus 2 activity used alone or previously used.

The pharmaceutical composition according to the present disclosure may comprise a pharmaceutically acceptable carrier and may be formulated for oral or parenteral human or veterinary use. When formulating the pharmaceutical composition according to the present disclosure, diluents or excipients such as fillers, extenders, binders, wetting agents, disintegrants and surfactants may be used. Solid manufactures for oral administration comprise tablets, pills, powders, granules and capsules. These solid manufactures are prepared by mixing at least one excipient, such as starch, calcium carbonate, sucrose or lactose, and gelatin, with the pharmaceutical composition comprising the compound according to the present disclosure. In addition, in addition to simple excipients, lubricants such as magnesium, sterate, and talc may be used. Liquid manufactures for oral use comprise suspensions, liquid solutions, emulsions and syrups, and may comprise various excipients, such as wetting agents, sweeteners, fragrances and preservatives, in addition to water and liquid paraffin, which are commonly used simple diluents. Formulations for parenteral administration comprise sterilized aqueous solutions, non-aqueous solutions, suspensions, emulsions, lyophilized formulations, and suppositories. The non-aqueous solvent and the suspension solvent may comprise vegetable oils such as propylene glycol, polyethylene glycol and olive oil, and injectable esters such as ethyl oleate. A base for suppositories may comprise witepsol, macrogol, tween 61, cacao butter, laurin, glycerogelatin, and the like.

In "hydrate" in the present disclosure, the compound represented by the Chemical Formula 1 or the compound represented by the Chemical Formula 2 is bound to water in non-covalently and via an intermolecular force. The hydrate may comprise a stoichiometric or non-stoichiometric amount of water. Specifically, the hydrate may comprise water in a ratio of about 0.25 mol to about 10 mol, more specifically, about 0.5 mol, about 1.5 mol, about 2 mol, about 2.5 mol, about 3 mol, etc. based on 1 mol of the active ingredient. However, the disclosure is not limited thereto.

In the "solvate" in the present disclosure, the compound represented by the Chemical Formula 1 or the compound represented by the Chemical Formula 2 is bound to a solvent other than water via an intermolecular force. The solvate may comprise a stoichiometric or non-stoichiometric amount of the solvent. Specifically, the solvate may comprise the solvent in a ratio of about 0.25 mol to about 10 mol, more specifically, about 0.5 mol, about 1.5 mol, about 2 mol, about 2.5 mol, about 3 mol, or about 5 mol, etc. based on 1 mol of the active ingredient. However, the disclosure is not limited thereto.

The pharmaceutical composition according to the present disclosure may be administered orally or parenterally according to the intended method. For parenteral administration, it is preferable to select an injection method for external use of the skin or intraperitoneal injection, rectal injection, subcutaneous injection, intravenous injection, intramuscular injection or intrathoracic injection.

Further, the pharmaceutical composition according to the present disclosure may be administered by inhalation. When the medicament is delivered directly to the lungs, it does not show toxicity and may exhibit a longer duration of action at a smaller dose. Administration for inhalation may be administration using a pharmaceutical formulation inhalable through the airways, nasal passages, etc., comprising respirable particles or droplets comprising a medicament. For such inhalation administration, but not limited thereto, for example, one of a dry powder inhaler (DPI) or a pressurized metered dose inhaler (pMDI) may be used. The medicament particles are lightly compressed into a frangible matrix comprised within, for example, a delivery device (dry powder inhaler). In operation, the delivery device abrades some of the medicament particles from the matrix and disperses them into an inhaled breath that delivers the medicament particles to the airways. Alternatively, the medicament particles may be a free-flowing powder comprised inside a reservoir in a delivery device (dry powder inhaler). The reservoir may be an integral chamber inside the device, or a capsule, blister, or similar capacity reservoir that is inserted into the device prior to operation. In operation, the device disperses some of the medicament particles from the reservoir and disperses them into the inhaled breath that delivers the medicament particles to the airways.

The pharmaceutical composition according to the present disclosure may be administered to a subject to prevent or treat severe acute respiratory syndrome coronavirus 2 infection or a disease caused by severe acute respiratory syndrome coronavirus 2. The term "subject" or "target" as used in the present disclosure refers to mammals such as horses, sheep, pigs, goats, and dogs, comprising humans having a severe acute respiratory syndrome coronavirus 2 infection or a disease caused by severe acute respiratory syndrome coronavirus 2 and having symptoms which may be reduced via administering the pharmaceutical composition according to the present disclosure thereto. The subject preferably refers to humans.

The term "administration", as used in the present disclosure, means introducing a pharmaceutical composition according to the present disclosure to a subject in any suitable way. The composition may be administered orally or parenterally through any general route as long as the composition may reach the intended tissue via the route of the administration. Further, the pharmaceutical composition according to the present disclosure may be administered by any device as long as the composition moves to the target cell.

The pharmaceutical composition according to the present disclosure is administered in a pharmaceutically effective amount. The term used in the present disclosure "the pharmaceutically effective amount" means an amount sufficient to treat a disease with a reasonable benefit/risk ratio applicable to medical treatment. Effective dosage levels may be determined depending on factors comprising the patient's weight, sex, age, health status, severity, activity of the medicament, sensitivity to the medicament, time of administration, route of administration and rate of excretion, duration of treatment, concurrent medicaments and other well-known factors in medical fields. The pharmaceutical composition according to the present disclosure may be administered as an individual treatment agent or may be administered in combination with other treatment agents, and may be administered sequentially or simultaneously with conventional treatment agents, and may be administered single or multiple times. It is important to take into account all of the above factors and then administer the minimum amount at which the maximum effect may be obtained without side effects based on the considerations. This amount may be easily determined by a person skilled in the art.

For example, in the pharmaceutical composition according to the present disclosure, the compound represented by the Chemical Formula 1 or a pharmaceutically acceptable salt thereof may be administered in 0.0001 to 500 mg/kg, preferably 0.001 to 100 mg/kg. The above administration amount may be administered once or several times a day.

Further, for example, in the pharmaceutical composition according to the present disclosure, the compound represented by the Chemical Formula 2 or a pharmaceutically acceptable salt thereof may be administered in a dose of 0.0001 to 500 mg/kg, preferably 0.001 to 100 mg/kg. The administration amount may be administered once or several times a day.

Further, for example, in the pharmaceutical composition according to the present disclosure, the compound represented by the Chemical Formula 1 or a pharmaceutically acceptable salt thereof, and the compound represented by the Chemical Formula 2 or a pharmaceutically acceptable salt thereof may be administered in a combination of the above-mentioned appropriate dosage range.

The pharmaceutical composition according to the present disclosure may further comprise one or more active ingredients exhibiting the same or similar medicinal effects in addition to the compound represented by the Chemical Formula 1 and/or the compound represented by the Chemical Formula 2.

The present disclosure provides a method for preventing or treating severe acute respiratory syndrome coronavirus 2 infection or diseases caused by severe acute respiratory syndrome coronavirus 2 infection, the method comprising administering a therapeutically effective amount of the composition comprising the compound represented by the Chemical Formula 1, the compound represented by the Chemical Formula 2, or a combination of the compound represented by the Chemical Formula 1 and the compound represented by the Chemical Formula 2, to a subject in need thereof.

The term "therapeutically effective amount" used in the present disclosure refers to an amount of the compound represented by the Chemical Formula 1 or a pharmaceutically acceptable salt thereof; or an amount of the compound represented by the Chemical Formula 2, or a pharmaceutically acceptable salt thereof; or an amount of the combination of the compound represented by the Chemical Formula 1 or a pharmaceutically acceptable salt thereof, and the compound represented by the Chemical Formula 2 or a pharmaceutically acceptable salt thereof, which is effective in preventing or treating severe acute respiratory syndrome coronavirus 2 infection or diseases caused by severe acute respiratory syndrome coronavirus 2 infection.

The present disclosure provides a method for treating severe acute respiratory syndrome coronavirus 2 infection disease, the method comprising administering a therapeutically effective amount of the compound represented by the Chemical Formula 2; or a combination of the compound represented by the Chemical Formula 1 and the compound represented by the Chemical Formula 2 to a subject in need thereof.

When administering the composition comprising the compound represented by the Chemical Formula 1 or the compound represented by the Chemical Formula 2, not only the disease itself is treated before the expression of the symptom, but also the symptom thereof is inhibited or avoided. In the management of the disease, the prophylactic or therapeutic dose of a particular active ingredient will vary depending on the nature and severity of the disease or condition, and the route through which the active ingredient is administered. The dose and frequency of dose will vary depending on the age, weight and response of the individual patient. A suitable dosage regimen may be readily selected by one of ordinary skill in the art upon taking these factors into account.

The subject may be a mammal, comprising humans.

The treatment method may further comprise administration of a therapeutically effective amount of an additional active agent that is helpful in disease treatment in combination with the composition comprising the compound represented by the Chemical Formula 1; the compound represented by the Chemical Formula 2; or the combination of the compound represented by the Chemical Formula 1 and the compound represented by the Chemical Formula 2. The additional active agent may exhibit a synergistic effect or an auxiliary effect together with the composition comprising the compound represented by the Chemical Formula 1 or the compound represented by the Chemical Formula 2.

The present disclosure is intended to provide a use of the composition comprising the compound represented by the Chemical Formula 1; the compound represented by the Chemical Formula 2; or a combination of the compound represented by the Chemical Formula 1 and the compound represented by the Chemical Formula 2, for manufacture of a medicament for treatment of severe acute respiratory syndrome coronavirus 2 infection or diseases caused by severe acute respiratory syndrome coronavirus 2 infection. The compound represented by the Chemical Formula 1 or 2 for the manufacture of the medicament may be mixed with acceptable adjuvants, diluents, and carriers, and may be used in combination with other active agents to have a synergistic effect of the active ingredients.

The present disclosure provides the compound represented by the Chemical Formula 1; the compound represented by the Chemical Formula 2; or the combination of the compound represented by the Chemical Formula 1 and the compound represented by the Chemical Formula 2, for the treatment of severe acute respiratory syndrome coronavirus 2 infection disease.

The present disclosure provides a pharmaceutical composition for use in the prevention or treatment of severe acute respiratory syndrome coronavirus 2 infection disease, the composition comprising the compound represented by the Chemical Formula 1; the compound represented by the Chemical Formula 2; or the compound represented by the Chemical Formula 1 and the compound represented by the Chemical Formula 2 as the active ingredient.

In another aspect of the present disclosure, there is provided an anti-severe acute respiratory syndrome coronavirus 2 composition comprising the compound represented by the Chemical Formula 1, or a pharmaceutically acceptable salt thereof, as an active ingredient.

In another aspect of the present disclosure, there is provided an anti-severe acute respiratory syndrome coronavirus 2 composition comprising a compound represented by the Chemical Formula 2, or a pharmaceutically acceptable salt thereof, as an active ingredient.

In another aspect of the present disclosure, there is provided an anti-severe acute respiratory syndrome coronavirus 2 composition comprising the compound represented by the Chemical Formula 1, or a pharmaceutically acceptable salt thereof; and a compound represented by the Chemical Formula 2, or a pharmaceutically acceptable salt thereof, as an active ingredient.

In another aspect of the present disclosure, there is provided an inhibitor for inhibiting activity of 3CL protease, the inhibitor comprising the compound represented by the Chemical Formula 1, or a pharmaceutically acceptable salt thereof.

In another aspect of the present disclosure, there is provided an inhibitor for inhibiting activity of 3CL protease, the inhibitor comprising the compound represented by the Chemical Formula 2, or a pharmaceutically acceptable salt thereof.

In another aspect of the present disclosure, there is provided an inhibitor for inhibiting activity of 3CL protease, the inhibitor comprising the compound represented by the Chemical Formula 1, or a pharmaceutically acceptable salt thereof, and the compound represented by the Chemical Formula 2, or a pharmaceutically acceptable salt thereof.

Since the amino acid sequence and structure of 3CLpro has little change between viruses and, above all, the function of 3CLpro is essential for viral proliferation, 3CLpro may be used as one of the important targets of virus treatment agents.

According to the present disclosure, the compound represented by the Chemical Formula 1; the compound represented by the Chemical Formula 2; or the combination of the compound represented by the Chemical Formula 1 and the compound represented by the Chemical Formula 2 has an excellent inhibitory effect on the activity of 3CL protease.

As may be identified above, Zafirlukast; Sulfinpyrazone; and the combination of Zafirlukast and Sulfinpyrazone according to the present disclosure may exhibit very excellent amelioration effects in terms of lung lesions, and thus may show rapid treatment and amelioration effects for the infection.

The matters mentioned in the use, composition and treatment method according to the present disclosure are the same as long as they are not contradictory to each other.

In another aspect of the present disclosure, the present disclosure provides a food composition for preventing or ameliorating severe acute respiratory syndrome coronavirus 2 infection disease, the composition comprising a compound represented by a following Chemical Formula 1, or a food acceptable salt thereof.

[Chemical Formula 1]

In another aspect of the present disclosure, the present disclosure provides a food composition for preventing or ameliorating severe acute respiratory syndrome coronavirus 2 infection disease, the composition comprising a compound represented by a following Chemical Formula 2, or a food acceptable salt thereof.

[Chemical Formula 2]

In another aspect of the present disclosure, the present disclosure provides a food composition for preventing or ameliorating severe acute respiratory syndrome coronavirus 2 infection disease, the composition comprising the compound represented by the following Chemical Formula 1, or a food acceptable salt thereof; and the compound represented by the following Chemical Formula 2, or a food acceptable salt thereof.

[Chemical Formula 1]

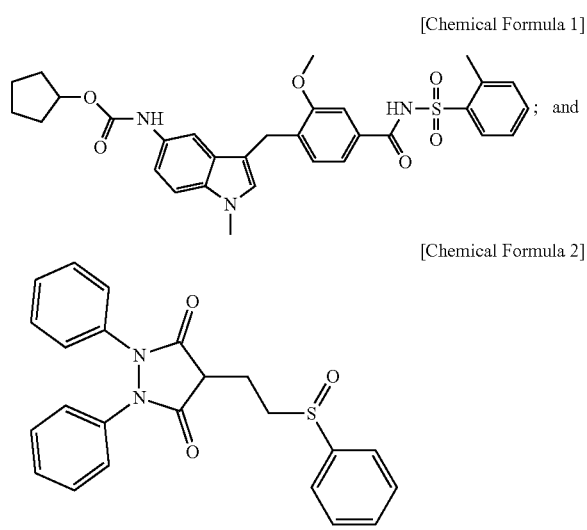

[Chemical Formula 2]

All of the contents above-described with reference to the pharmaceutical compositions may be equally applied to the compound represented by the Chemical Formula 1, or a pharmaceutically acceptable salt thereof; and the compound represented by the Chemical Formula 2 or a pharmaceutically acceptable salt thereof.

In the present disclosure, the food composition may be added as it is or used with other foods or food ingredients, and may be suitably used according to a conventional method.

In the present disclosure, the "food composition" refers to a food produced and processed using raw materials or ingredients having useful functions for the human body.

There is no particular limitation on the type of food. Examples of foods that may be added to the composition comprising the compound represented by the Chemical Formula 1, or a food acceptable salt thereof may comprise various soups, beverages, tea, drinks, alcoholic beverages and vitamin complexes, may comprise all health foods in the usual sense. In addition to the above listed foods, the composition comprising the compound represented by the Chemical Formula 1 according to the present disclosure, or a food acceptable salt thereof, may comprise various nutrients, vitamins, electrolytes, flavoring agents, colorants, pectic acid and salts thereof, alginic acid and salts thereof, organic acids, protective colloidal thickeners, pH adjusters, stabilizers, preservatives, glycerin, alcohols, carbonates used in carbonated beverages, and the like. In addition, the food composition according to the present disclosure may comprise fruit flesh for production of natural fruit juice, fruit juice drink and vegetable drink. These ingredients may be used independently or in combination with each other.

Advantageous Effects

The pharmaceutical composition according to the present disclosure has an effect of preventing or treating severe acute respiratory syndrome coronavirus 2 infection or a disease caused by severe acute respiratory syndrome coronavirus 2.

The food composition according to the present invention has an effect of preventing or ameliorating severe acute respiratory syndrome coronavirus 2 infection or a disease caused by severe acute respiratory syndrome coronavirus 2.

DESCRIPTION OF DRAWINGS

FIG. 1 shows an AI deep learning algorithm based on an AI novel medicament platform (DeepMatcher™).

FIG. 2 is a graph showing the results of the cytotoxicity evaluation and cytopathic inhibition efficacy of the compounds of the Chemical Formula 1 and Chemical Formula 2 according to the present disclosure.

FIG. 3 shows the observation results of cell morphology before and after treatment of the compounds of the Chemical Formula 1 and Chemical Formula 2 according to the present disclosure.

FIG. 4 shows the 3CL protease activity results of the compounds of the Chemical Formula 1 and Chemical Formula 2 according to the present disclosure.

FIG. 5 shows the results of medicament efficacy evaluation for ACE2 and SARS-CoV-2 Spike 51 protein binding activity of compounds of the Chemical Formulas 1 and 2 according to the present disclosure.

FIG. 6 shows the lung structure divided into ① to ② portions according to the lung lobes, and shows the criteria for evaluating lung lesions based on weights thereof.

FIG. 7 is a diagram showing the result of identifying a gross cure rate. NC (Negative control), VC (Virus control), PC (Positive control, Remdesivir), Za (Zafirlukast), Za+Sulf (Zafirlukast and Sulfinpyrazone).

FIG. 8 shows the gross lung lesions as identified by performing the experiment.

MODES OF THE INVENTION

Examples are presented to help understand the present disclosure. The following examples are provided for easier understanding of the present disclosure, and the contents of the present disclosure are not limited by the examples.

<Production Example 1> Zafirlukast

Commercially available Zafirlukast (CAS Number: 107753-78-6) was used.

<Manufacture Example 2> Sulfinpyrazone

Commercially available Sulfinpyrazone (CAS Number: 57-96-5) was used.

<Manufacture Example 3> Combination of Zafirlukast and Sulfinpyrazone

The Zafirlukast and Sulfinpyrazone were used in combination with each other.

<Example 1> Screening of Candidate Compounds that Inhibit Severe Acute Respiratory Syndrome Coronavirus 2 3CL Protease According to the present disclosure, we searched for 3CL protease inhibitory compounds and derived candidate medicaments therefrom, from 2,700 FDA-approved medicaments (source: https://www.medicamentbank.ca/), using an AI deep learning algorithm based on an AI novel medicament platform (DeepMatcher™), based on information about the protein-ligand complex structure of severe acute respiratory syndrome coronavirus 2 3CL protease (Protein Data Bank ID 6LU7: The crystal structure of severe acute respiratory syndrome coronavirus 2 main protease in complex with an inhibitor N3, DOI: 10.2210/pdb6LU7/pdb). The 3D-virtual graphic simulation method based on the AI novel medicament platform (DeepMatcher™) used in the present disclosure allows the interaction of the protein-ligand complexe to be simulated according to changes in the actual physical environment (changes in the molecules structure, state, and physical properties). Using the 3D-virtual graphic simulation method, we analyzed and measured the number of moving snapshots of medicament molecules that bind via the binding force of various compounds on the ligand binding site of the protein, and predicted the binding frequency (HBQI: high binding quality index) and the binding structure similarity (RMSD: Root Mean Square Deviation), etc. (FIG. 1).

<Example 2> SARS CoV-2 Antiviral (Cell Lesion Inhibitory Ability) Medicament Evaluation Material (medicament): Zafirlukast, Sulfinpyrazone
Test virus and cell line: 1 type SARS CoV-2 (NCCP-43326), VERO cell
Test concentration and number of repetitions: 2 Dose (10 to 20 μM)/2 repetitions Example 2-1: Cell Cytotoxicity Assay DMEM (5% FBS, 1% Antibiotic-Antimycotic) was used as the cell culture solution. Cytotoxicity evaluation for the test sample (medicament) was tested by MTT assay. Further, the solvent (DMSO) used when preparing the sample based on a test concentration was used at a final concentration of 0.5% or lower.

Cytotoxicity evaluation was performed in a following order.

1) After dispensing cells into a 96 well plate at $5 \times 10^4$ cells/well per well, the cells for 48 hours in a 37° C., 5% $CO_2$ incubator were incubated, a cell monolayer was obtained, and then washed twice with PBS.

2) Samples (medicaments) prepared based on the test concentrations together with the culture medium were dispensed at 100 μL/well, and the cells were cultured for 72 hours in a 37° C., 5% $CO_2$ incubator.

3) After the cell state was identified, 10 μL/well of MTT solution was added thereto, and then the cells were stationary for 4 hours in a 37° C., 5% $CO_2$ incubator.

4) After 4 hours reaction, 100 μL/well of MTT solution was added thereto, and the formazan crystals were sufficiently dissolved using a pipet, and the absorbance thereof was measured at 570 nm with a plate reader.

5) The cytotoxicity ratio was calculated according to Equation 1 below as the ratio of the normal cells and the group treated with the test sample (medicament).

$$\text{Cell viability (\%)} = \text{Test OD/Control OD} \times 100\% \qquad \text{<Equation 1>}$$

Example 2-2: CPE Reduction Test (Evaluation of Cytopathic Inhibition efficacy)

The evaluation of the cytopathic inhibition efficacy was carried out in the following manner.

1) After dispensing cells into a 96 well plate at $5 \times 10^4$ cells/well per well, the cells for 48 hours in a 37° C., 5% $CO_2$ incubator were incubated, a cell monolayer was obtained, and then washed twice with PBS, and cell counting was performed.

2) Viruses were dispensed at 100 μL/well using DMEM (FBS free, 1% antibiotic-antimycotic) medium to infect 0.001 MOI, and the cells were stationary for 1 hour in a 37° C., 5% $CO_2$ incubator.

3) After 1 hour of infection, virus was removed, samples (medicaments) prepared based on test concentrations together with the culture medium were dispensed at 100 μL/well, and the cells were cultured for 72 hours in a 37° C., 5% $CO_2$ incubator.

4) After the cell state was identified, 10 μL/well of MTT solution was added thereto and the cells were stationary for 4 hours in a 37° C., 5% $CO_2$ incubator.

5) After 4 hours reaction, 100 μL/well of MTT solution was added thereto, and the formazan crystals were sufficiently dissolved using a pipet, and the absorbance thereof was measured at 570 nm with a plate reader.

6) The cytotoxicity ratio was calculated according to Equation 2 below as the ratio of the normal cells and the group treated with the test sample (medicament).

$$\text{Virus inhibition rate (\%)} = (\text{Test OD} - \text{Virus OD})/(\text{Control OD} - \text{Virus OD}) \times 100\% \qquad \text{<Equation 2>}$$

The cytotoxicity-based anti-severe acute respiratory syndrome coronavirus 2 efficacy evaluation results identified according to Example 2-1 and Example 2-2 are shown in Table 1 and FIG. 2 below.

TABLE 1

| Medicament name | Viability | | CPE Reduction (%) | |
| --- | --- | --- | --- | --- |
| | 10 μM | 20 μM | 10 μM | 20 μM |
| Zafirlukast | 109.7 ± 2.8 | 89.3 ± 0.7 | 60.1 ± 7.1 | 75.6 ± 3.9 |
| Sulfinpyrazone | 108.3 ± 0.4 | 99.6 ± 7.3 | 33.1 ± 7.0 | 40.7 ± 8.0 |

Based on a result of performing anti-severe acute respiratory syndrome coronavirus 2 efficacy evaluation, referring to Table 1 and FIG. 2, both Zafirlukast and/or Sulfinpyrazone medicaments exhibited excellent cell survival. It was confirmed that for Zafirlukast at 20 μM, the CPE reduction was 75.6±3.9% and for Sulfinpyrazone at 20 μM, the CPE reduction was 40.7±8.0%, which means that Zafirlukast and Sulfinpyrazone medicaments have the effect of inhibiting cytopathic effect.

<Example 3> Observation of Cell Morphology According to Medicament Treatment

Material (medicament): Zafirlukast, Sulfinpyrazone
Test virus and cell line: 1 type SARS CoV-2 (NCCP-43326), VERO cell
Test concentration and number of repetitions: 2 Dose (10 to 20 μM)/2 repetitions For each of the cells before and after the virus treatment, changes in cell morphology that occurred when the cell was treated with the medicament were observed. The results are shown in FIG. 3.

As may be seen in FIG. 3, it may be identified that in the control group, the virus-infected cells (Virus) has the morphology change greater than that of the virus-non-infected cells (Normal).

On the other hand, it may be discerned that the morphology change was small in each experimental group in which virus-infected cells were treated with Zafirlukast and Sulfinpyrazone.

<Example 4> 3CL Protease (3-Chymotrypsin-Like Protease) Inhibition Efficacy Assay Material (medicament): Zafirlukast, Sulfinpyrazone Test 3CL Protease:

GC376 is purchased from Aobious (catalog number A0B36447)

3CL Protease Assay Buffer (BPS catalog number 79956)

3CL Protease Substrate (BPS catalog number 79952)

Test concentration and number of repetitions; 10 Dose (0.001 to 30 µM)/2 repetitions The analysis of the 3CL Protease inhibition efficacy using the time-resolved fluorescence resonance energy transfer assay was carried out as follows.

1) Each medicament was dissolved in 100% DMSO at a concentration of 10 mM, and the intermediate dilution process was carried out while maintaining the 100% DMSO concentration.

2) After diluting the compound by 67.5 times with 3CL Protease Assay buffer, a 50 ul response solution having a DMSO concentration of 0.3% was prepared with 10 ul of the diluted sample and 40 ul of the buffer.

3) Each medicament was stationary at room temperature for 30 minutes, and mixing thereof was carried out so that the final concentration of the substrate of 3CL protease was 50 uM.

4) The reactant reacted at room temperature for more than 12 hours.

5) Then, the TR-FRET signal was read from the Infinite M1000 microplate reader (Tecan).

The results of medicament efficacy evaluation on the activity of the SARS-CoV-2 3CL protease protein as identified accordingly are shown in Tables 2 and 3, and FIG. 4 below.

TABLE 2

| Zafirlukast | 3 CL Protease Activity (Fluorescence count) | | % Activity | |
|---|---|---|---|---|
| [µM] | Repeat 1 | Repeat 2 | Repeat 1 | Repeat 2 |
| No Compound | 919 | 897 | 101 | 99 |
| 0.001 | 909 | 869 | 100 | 95 |
| 0.003 | 869 | 889 | 95 | 98 |
| 0.01 | 862 | 929 | 94 | 103 |
| 0.03 | 883 | 902 | 97 | 99 |
| 0.1 | 870 | 908 | 95 | 100 |
| 0.3 | 867 | 895 | 95 | 98 |
| 1 | 828 | 863 | 90 | 94 |
| 3 | 818 | 805 | 89 | 87 |
| 10 | 730 | 723 | 78 | 77 |
| 30 | 525 | 552 | 52 | 55 |
| Background | 107 | 110 | — | — |

TABLE 3

| (±)-Sulfinpyrazone | 3 CL Protease Activity (Fluorescence count) | | % Activity | |
|---|---|---|---|---|
| [µM] | Repeat 1 | Repeat 2 | Repeat 1 | Repeat 2 |
| No Compound | 1030 | 985 | 103 | 97 |
| 0.001 | 970 | 1015 | 96 | 101 |
| 0.003 | 1045 | 1018 | 104 | 101 |
| 0.01 | 1010 | 1014 | 100 | 101 |
| 0.03 | 1033 | 1030 | 103 | 103 |
| 0.1 | 1030 | 1005 | 103 | 100 |
| 0.3 | 1024 | 952 | 102 | 94 |
| 1 | 998 | 994 | 99 | 98 |
| 3 | 935 | 964 | 92 | 95 |
| 10 | 914 | 964 | 90 | 95 |
| 30 | 848 | 830 | 82 | 80 |
| Background | 108 | 117 | — | — |

Referring to Tables 2, and 3, and FIG. 4, it was identified that the activity of 3CL protease was inhibited by about 45% or more at a concentration of 30 µM of Zafirlukast. At a concentration of 30 µM of sulfinpyrazone, the activity of 3CL protease was found to be inhibited by about 20%. Therefore, it was identified that Zafirlukast and/or Sulfinpyrazone was effective in inhibiting 3-chymotrypsin-like protease activity.

<Example 5> Evaluation of Medicament Efficacy for ACE2 and SARS-CoV-2 Spike S1 Protein Binding Activity Via CE2:Spike S1 Time-Resolved Fluorescence Resonance Energy Transfer Analysis Material (medicament): Zafirlukast, Sulfinpyrazone Test ACE2 and Spike 51 proteins:

ACE2, His-Tag, Eu-labeled (BPS Bioscience, 100705)

Spike S1, Fc fusion, Avi-tag, Biotin Labeled (SARS-CoV-2) (BPS Bioscience, 100679)

Anti-Spike, Neutralizing Antibody (Active Motif, 91361)

Test concentration and number of repetitions; 10 Dose (0.002 to 30 µM)/2 repetitions ACE2:Spike 51 time-resolved fluorescence resonance energy transfer analysis was performed in the following manner.

1) ACE2-Eu was diluted to 1 ng/uL (12 nM) using 1×ACE2-Spike TR-FRET buffer, and then 5 uL thereof was dispensed into each well.

2) After diluting the Dye-labeled receptor 100 times with 1×ACE2-Spike TR-FRET buffer, 5 uL of the diluted Dye-labeled receptor was added to each well.

3) 5 uL of each of samples (medicaments) prepared for test concentrations was added to the well.

4) After diluting Spike S1-Biotin to 20 ng/uL (200 nM) using 1×ACE2-Spike TR-FRET buffer, 5 uL of Spike S1-Biotin as diluted was added to each of wells designated as test and control groups.

5) 5 uL of 1×ACE2-Spike TR-FRET buffer was added to remaining wells to which Spike S1-Biotin was not added. The plate was incubated for 1 hour at room temperature.

6) Then, the TR-FRET signal was read from the Infinite M1000 microplate reader (Tecan).

The results of medicament efficacy evaluation for the ACE2 and SARS-CoV-2 Spike S1 protein binding activity as identified accordingly are shown in Tables 4, and 5 below, and FIG. 5.

TABLE 4

| Zafirlukast | Tr-FRET ratio | | % Activity | |
|---|---|---|---|---|
| [µM] | Repeat 1 | Repeat 2 | Repeat 1 | Repeat 2 |
| No compound | 0.97 | 0.96 | 101 | 99 |
| 0.002 | 0.90 | 0.94 | 91 | 97 |
| 0.005 | 0.94 | 0.92 | 96 | 94 |
| 0.014 | 0.91 | 0.93 | 92 | 95 |
| 0.041 | 0.96 | 0.93 | 99 | 95 |
| 0.123 | 0.95 | 0.94 | 97 | 96 |
| 0.370 | 0.97 | 0.93 | 101 | 95 |
| 1.111 | 0.92 | 0.94 | 93 | 96 |
| 3.333 | 0.98 | 0.96 | 102 | 99 |
| 10 | 0.94 | 0.95 | 96 | 98 |
| 30 | 0.93 | 0.94 | 95 | 96 |
| Blank | 0.27 | 0.27 | 0 | 0 |

TABLE 5

| (±)-Sulfinpyrazone | TR-FRET ratio | | % Activity | |
|---|---|---|---|---|
| [µM] | Repeat 1 | Repeat 2 | Repeat 1 | Repeat 2 |
| No compound | 0.97 | 0.96 | 101 | 99 |
| 0.002 | 0.94 | 0.93 | 96 | 95 |
| 0.005 | 0.94 | 0.94 | 97 | 96 |
| 0.014 | 0.97 | 0.94 | 100 | 97 |
| 0.041 | 0.95 | 0.96 | 98 | 99 |
| 0.123 | 0.96 | 0.97 | 100 | 101 |
| 0.370 | 0.96 | 0.95 | 99 | 98 |
| 1.111 | 0.97 | 0.96 | 101 | 100 |
| 3.333 | 0.95 | 0.97 | 98 | 101 |
| 10 | 0.96 | 0.93 | 100 | 95 |
| 30 | 0.96 | 0.94 | 99 | 96 |
| Blank | 0.27 | 0.27 | | |

Referring to Table 4, Table 5 and FIG. 5, Zafirlukast and Sulfinpyrazone were identified as having no efficacy in inhibiting the binding of ACE2 and Spike 51 proteins. That is, it was identified that Zafirlukast and Sulfinpyrazone do not belong to medicaments that bind to ACE2 and Spike 51 to exhibit an action effect, but belong to a medicament that may exhibit disease treatment effects via inhibition of 3CL protease.

<Example 6> Medicament Efficacy Evaluation in Severe Acute Respiratory Syndrome Coronavirus 2 Infection Animal Model Using Syrian Hamster A Syrian Hamster animal model was used to identify the effect of treatment of the medicaments on severe acute respiratory syndrome coronavirus 2 infection.

The experiment was carried out according to the conditions of Table 6 below.

TABLE 6

| Hamsters | Female, 5 n/groups |
|---|---|
| Age | About one month aged |
| Virus Titer | $2.0 \times 10^5$ PFU/mL |
| Inoculate Route | Intranasal (100 µL) |
| Medicament Administration | per oral (PO, 500 µL) |

The experiment was performed by administering severe acute respiratory syndrome coronavirus 2 to the animal model according to the above conditions. The conditions for the test group are shown in Table 7 below:

TABLE 7

| No. | Group (n = 5) | | Dose | Vehicle | Administration | Others |
|---|---|---|---|---|---|---|
| 1 | Test common | Negative control (NC) | | | | |
| 2 | Test common | Virus control (VC) | | | | |
| 3 | Test common | Control (Remdesivir) (PC) | 5 mg/kg/day | Water (Suspension) | IP, once a day | Administered simultaneously with virus infection |
| 4 | Alone | Zafirlukast (Za) | 60 mg/kg/day | Water (Suspension) | PO twice daily (30 mg/kg, twice) | Administered simultaneously with virus infection |
| 5 | Combined | Zafirlukast and Sulfinpyrazone (Z + S) (Za + Sulf) | 60 mg/kg/day and 120 mg/kg/day | Water (Suspension) | PO twice daily (30 mg/kg, twice) and PO twice daily (60 mg/kg, twice) | Administered simultaneously with virus infection |

The experimental set was configured as above.

Respiratory anesthesia was performed for 10 minutes using Isoflurane. 100 µL of the prepared SARS-Cov-2 virus was instilled in the hamster nasal cavity to infect the nasal cavity, and then 500 µL of the prepared medicament was orally administered to the hamster using a sonde. The gross lung lesions were evaluated for lung tissue collected through autopsy on the 4th day (PID4) after infection. The gross lung lesion was calculated as the ratio of the virus group and the test group according to the following equation.

Specifically, as mentioned in FIG. 6, the lungs are divided into ① to ⑤ according to the lung lobe. Lung lesions were evaluated based on weights thereof. The criteria are shown in Table 8 below.

TABLE 8

| Lung lobe | % of lung weight (%) |
|---|---|
| 1 | 40 |
| 2 | 10 |
| 3 | 5 |
| 4 | 30 |
| 5 | 15 |
| Total area % | 100 |

According to the criteria in Table 8, a gross cure rate evaluation was performed. The result was identified based on the following Equation. The results are shown in FIG. 7.

Gross cure rate=pneumonia incidence rate in test group/pneumonia incidence rate in virus group× 100  <Equation 3>

FIG. 7 shows the gross cure rate. As may be seen in FIG. 7, when compared with the severe acute respiratory syndrome coronavirus 2 alone infection group (severe infection model, lung lesion 62%), the treatment efficacy at 5 days of continuous medicament administration was cure rate 94.3% for Zafirlukast (60 mg/kg/day)+Sulfinpyrazone (120 mg/kg/day), and cure rate 58.7% for Zafirlukast (60 mg/kg/day). In one example, the control medicament, Remdesivir (5 mg/kg/day) exhibited a cure rate of 44.3%. As may be seen above, Zafirlukast, and combination of Zafirlukast and Sulfinpyrazone according to the present disclosure exhibited superior treatment effect compared to the control medicament Remdesivir. Further, Zafirlukast, and combination of Zafirlukast and Sulfinpyrazone exhibited excellent amelioration in bilateral pneumonia, pulmonary edema, and pulmonary bleeding aspects. In particular, the combination of Zafirlukast and Sulfinpyrazone exhibited the best treatment efficacy clinically and did not exhibit abnormal findings or abnormal clinical symptoms.

Further, specifically, FIG. 8 shows the gross lung lesions as identified by performing the above experiment. In FIG. 8, the abbreviations are as follows: NC (Negative control), VC (Virus control), PC (Positive control), Za (Zafirlukast), Z+S (Zafirlukast and Sulfinpyrazone).

As may be seen above, Za (Zafirlukast) and Z+S (Zafirlukast and Sulfinpyrazone) according to the present disclosure exhibited very excellent amelioration effects in the gross lung lesion. In particular, it was identified that the combination of Zafirlukast and Sulfinpyrazone exhibited very good amelioration effects up to a level close to that of the normal control group.

<Example 7> Medicament Efficacy Evaluation of Sulfinpyrazone in a Severe Acute Respiratory Syndrome Coronavirus 2 Infected Animal Model Using Syrian Hamster The Syrian Hamster animal model was used to identify the treatment effect of Sulfinpyrazone on severe acute respiratory syndrome coronavirus 2 infection. The experiment was carried out according to the conditions of Table 9 below.

TABLE 9

| Hamsters | Female, 5 n/groups |
|---|---|
| Age | About 1 month aged |
| Virus Titer | $2.0 \times 10^5$ PFU/mL |
| Inoculate Route | Intranasal (100 µL) |
| Medicament Administration | per oral (PO, 500 µL) |

The experiment was performed by administering severe acute respiratory syndrome coronavirus 2 to the model according to the above conditions. The conditions for the test group are shown in Table 10 below:

TABLE 10

| No. | Group (n = 5) | | Dose | Vehicle | Administration | Others |
|---|---|---|---|---|---|---|
| 1 | Test common | Negative control (NC) | | | | |
| 2 | Test common | Virus control (VC) | | | | |
| 3 | Alone | Sulfinpyrazone | 50 mg/kg/day | Water (Suspension) | PO twice daily | Medicament administration begins after virus infection (PID 0) 1 day to 4 day |

The experimental set was configured as above to evaluate the lung lesion. The gross cure rate evaluation method was performed in the same manner as in Example 6. The results are shown in Table 11 below.

TABLE 11

| | Negative control (NC) | Virus control (VC) | Sulfinpyrazone 50 MPK |
|---|---|---|---|
| Gross pneumonia lesion amelioration percentage (%) | 100 | 1 | 15.6 |

As may be seen in FIG. 11, which is the result of the analysis of the gross cure rate, compared with the severe acute respiratory syndrome coronavirus 2 alone infected group, the treatment efficacy at 4 days of continuous medicament administration was the cure rate 15.6% for Sulfinpyrazone (50 mg/kg/day).

As may be identified above, Sulfinpyrazone according to the present disclosure exhibited an amelioration effect in the gross cure rate aspect.

In the present disclosure, details of contents that may be sufficiently recognized and inferred by those with ordinary knowledge in the technical field of the present disclosure have been omitted. In addition to the specific examples described in the present disclosure, more various modifications are possible within the scope of not changing the technical idea or essential composition of the present disclosure. Therefore, the present disclosure may be implemented in a different way than specifically described and illustrated in the present disclosure. This difference may be understood by those with ordinary knowledge in the technical field of the present disclosure.

The invention claimed is:

1. A method for preventing or treating severe acute respiratory syndrome coronavirus 2 infection disease, the method comprising administering to a patient in need thereof a compound represented by a following Chemical Formula 1, or a pharmaceutically acceptable salt thereof; and a compound represented by a following Chemical Formula 2, or a pharmaceutically acceptable salt thereof:

[Chemical Formula 1]

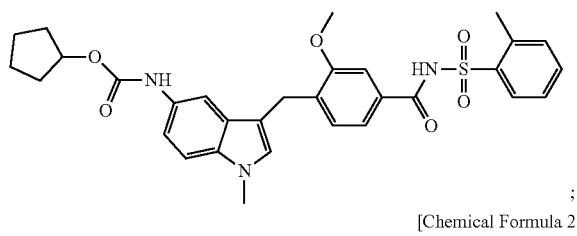

;

[Chemical Formula 2]

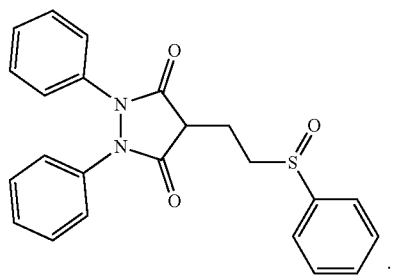

2. The method of claim 1, wherein the compound represented by the Chemical Formula 1 or the pharmaceutically acceptable salt thereof; and the compound represented by the Chemical Formula 2 or the pharmaceutically acceptable salt thereof are administered simultaneously, individually or sequentially in combination with each other.

3. The method of claim 1, wherein the compound represented by the Chemical Formula 1 or the pharmaceutically acceptable salt thereof; and the compound represented by the Chemical Formula 2 or the pharmaceutically acceptable salt thereof are administered simultaneously with each other.

4. The method of claim 1, wherein the compound represented by the Chemical Formula 1 or the pharmaceutically acceptable salt thereof; and the compound represented by the Chemical Formula 2 or the pharmaceutically acceptable salt thereof are administered individually.

5. The method of claim 1, wherein the compound represented by the Chemical Formula 1 or the pharmaceutically acceptable salt thereof; and the compound represented by the Chemical Formula 2 or the pharmaceutically acceptable salt thereof are administered sequentially.

6. The method of claim 1, wherein the compound represented by the Chemical Formula 1 or the pharmaceutically acceptable salt thereof; and the compound represented by the Chemical Formula 2 or the pharmaceutically acceptable salt thereof are administered orally.

7. The method of claim 1, wherein the severe acute respiratory syndrome coronavirus 2 infection disease is a respiratory disease.

8. The method of claim 1, wherein a symptom of the severe acute respiratory syndrome coronavirus 2 infection disease occurs after an incubation period of 2 to 14 days after the coronavirus infection.

9. The method of claim 1, wherein the severe acute respiratory syndrome coronavirus 2 infection disease exhibits at least one symptom selected from the group consisting of high fever, cough, shortness of breath, pneumonia, diarrhea, kidney failure, renal dysfunction and septic shock, by the severe acute respiratory syndrome coronavirus 2 infection.

10. A method for preventing or treating severe acute respiratory syndrome coronavirus 2 infection disease, the method comprising administering to a patient in need thereof a compound represented by a following Chemical Formula 1, or a pharmaceutically acceptable salt thereof:

[Chemical Formula 1]

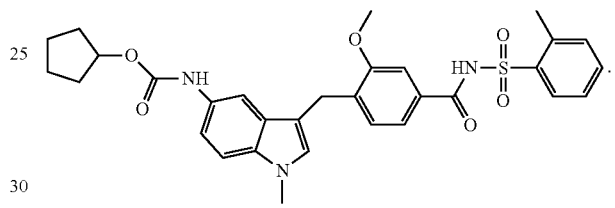

11. The method of claim 10, wherein the severe acute respiratory syndrome coronavirus 2 infection disease is a respiratory disease.

12. The method of claim 10, wherein a symptom of the severe acute respiratory syndrome coronavirus 2 infection disease occurs after an incubation period of 2 to 14 days after the coronavirus infection.

13. The method of claim 10, wherein the severe acute respiratory syndrome coronavirus 2 infection disease exhibits at least one symptom selected from the group consisting of high fever, cough, shortness of breath, pneumonia, diarrhea, kidney failure, renal dysfunction and septic shock, by the severe acute respiratory syndrome coronavirus 2 infection.

14. The method of claim 10, wherein the patient has been administered a compound of Chemical Formula 2 or a pharmaceutically acceptable salt thereof:

[Chemical Formula 2]

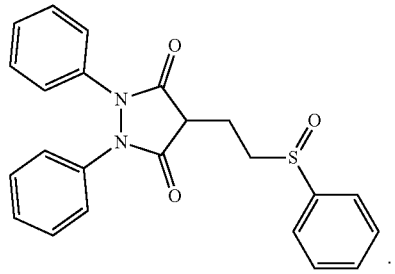

15. A method for preventing or treating severe acute respiratory syndrome coronavirus 2 infection disease, the method comprising administering to a patient in need thereof a compound represented by a following Chemical Formula 2, or a pharmaceutically acceptable salt thereof:

[Chemical Formula 2]

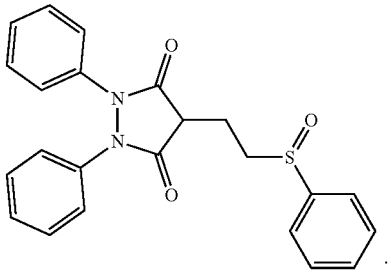

16. The method of claim 15, wherein the severe acute respiratory syndrome coronavirus 2 infection disease is a respiratory disease.

17. The method of claim 15, wherein a symptom of the severe acute respiratory syndrome coronavirus 2 infection disease occurs after an incubation period of 2 to 14 days after the coronavirus infection.

18. The method of claim 15, wherein the severe acute respiratory syndrome coronavirus 2 infection disease exhibits at least one symptom selected from the group consisting of high fever, cough, shortness of breath, pneumonia, diarrhea, kidney failure, renal dysfunction and septic shock, by the severe acute respiratory syndrome coronavirus 2 infection.

19. The method of claim 15, wherein the patient has been administered a compound of Chemical Formula 1, or a pharmaceutically acceptable salt thereof:

[Chemical Formula 1]

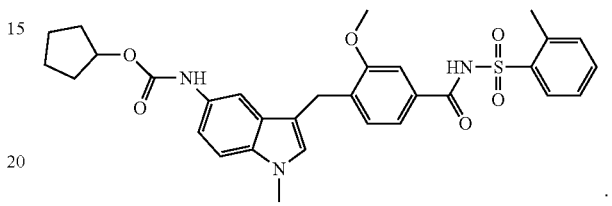

* * * * *